(12) United States Patent
Malawer

(10) Patent No.: US 9,084,614 B2
(45) Date of Patent: Jul. 21, 2015

(54) BONE RIFLING SYSTEM AND METHOD OF PREPARING A BONE USING SUCH SYSTEM

(71) Applicant: Martin M. Malawer, McLean, VA (US)

(72) Inventor: Martin M. Malawer, McLean, VA (US)

(73) Assignee: Orthorifling Systems, LLC, Falls Church, VA (US)

( * ) Notice: Subject to any disclaimer, the term of this patent is extended or adjusted under 35 U.S.C. 154(b) by 252 days.

(21) Appl. No.: 13/663,648

(22) Filed: Oct. 30, 2012

(65) Prior Publication Data
US 2013/0184709 A1 Jul. 18, 2013

Related U.S. Application Data

(62) Division of application No. 12/753,374, filed on Apr. 2, 2010, now Pat. No. 8,915,919.

(60) Provisional application No. 61/166,128, filed on Apr. 2, 2009.

(51) Int. Cl.
*A61B 17/16* (2006.01)

(52) U.S. Cl.
CPC ............ *A61B 17/16* (2013.01); *A61B 17/1617* (2013.01); *A61B 17/1659* (2013.01); *A61B 17/1684* (2013.01)

(58) Field of Classification Search
CPC ........... A61B 17/1617; A61B 17/1684; A61B 17/1659; A61B 17/16
USPC .................. 606/79, 80, 84, 86 R, 96–98, 183
See application file for complete search history.

(56) References Cited

U.S. PATENT DOCUMENTS

| 1,858,852 A | 5/1932 | Cleveland et al. |
| 3,037,406 A | 6/1962 | Fried |
| 3,996,625 A | 12/1976 | Noiles |
| 4,271,849 A | 6/1981 | Rehder |
| 4,462,394 A | 7/1984 | Jacobs |
| 4,550,788 A | 11/1985 | Park |

(Continued)

FOREIGN PATENT DOCUMENTS

| CN | 2221948 Y | 3/1996 |
| CN | 2469899 Y | 1/2002 |

OTHER PUBLICATIONS

"Notification of the First Office Action" issued by the State Intellectual Property Office of the People's Republic of China on Jan. 23, 2014, which corresponds to Chinese Patent Application No. 201080023436.2 and is related to U.S. Appl. No. 131663,648; with English language translation.

*Primary Examiner* — Andrew Yang
*Assistant Examiner* — Diana S Jones
(74) *Attorney, Agent, or Firm* — Studebaker & Brackett PC

(57) ABSTRACT

A bone rifling system for use in prosthesis, which allows improved prosthetic bone fixation. The system comprises orthopedic undercut reamer, which can cut controlled internal groove circles or spiral grooves on the internal surface of host bone. The system converts the commonly reamed smooth bone to grooved or rifled bony tube. Used together with bone cements, the bone rifling system ensures prosthetic bone fixation by significantly increasing the pull out strength, and decreasing the rate of clinical loosening and failure of replacement joints. Also disclosed is a method for preparing a bone for a prosthesis using such a bone rifling system to cut grooves in a host bone for increased prosthetic bone fixation.

15 Claims, 8 Drawing Sheets

(56) References Cited

U.S. PATENT DOCUMENTS

| | | | |
|---|---|---|---|
| 4,696,292 A * | 9/1987 | Heiple | 606/79 |
| 4,711,233 A | 12/1987 | Brown | |
| 5,387,218 A | 2/1995 | Meswania | |
| 5,441,538 A | 8/1995 | Bonutti | |
| 5,624,462 A | 4/1997 | Bonutti | |
| 5,653,712 A * | 8/1997 | Stern | 606/80 |
| 6,447,513 B1 | 9/2002 | Griggs | |
| 6,814,734 B2 | 11/2004 | Chappuis et al. | |
| 2005/0187555 A1 | 8/2005 | Biedermann et al. | |
| 2005/0216021 A1 | 9/2005 | Grimard et al. | |
| 2008/0161805 A1 | 7/2008 | Saravia et al. | |

* cited by examiner

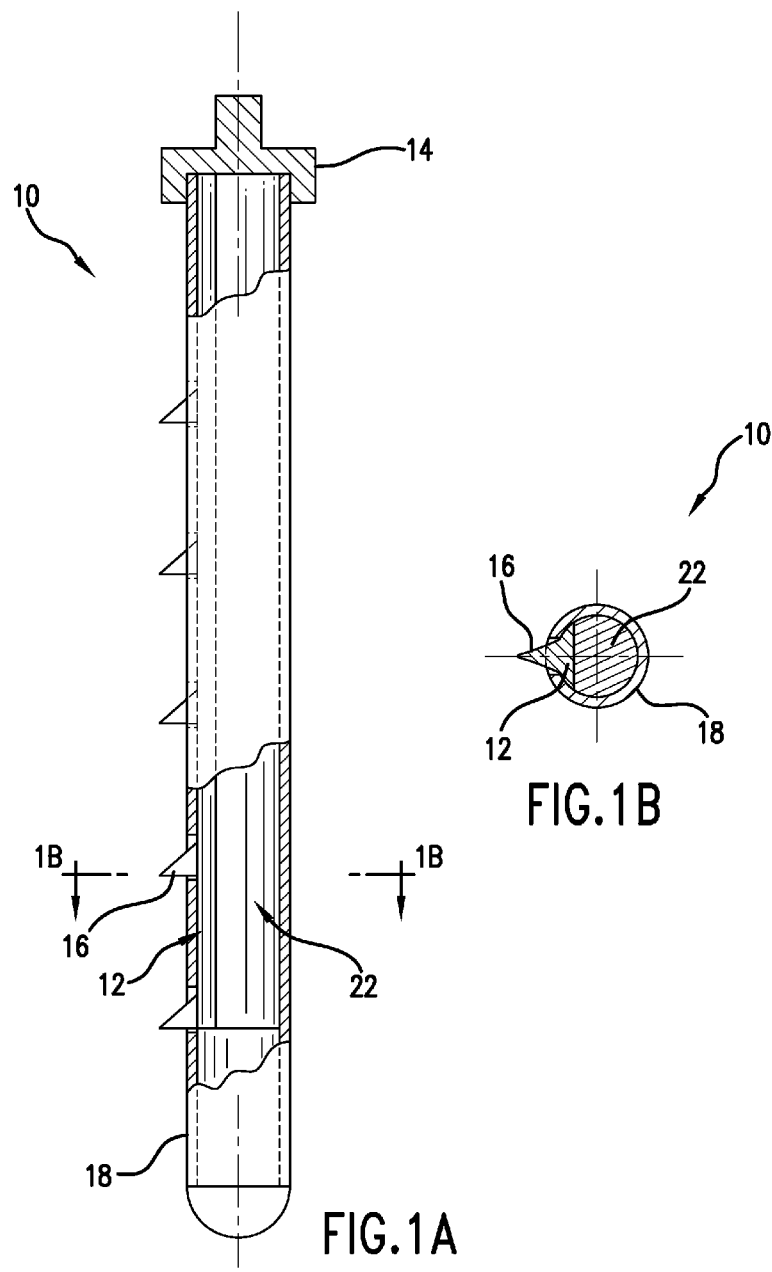

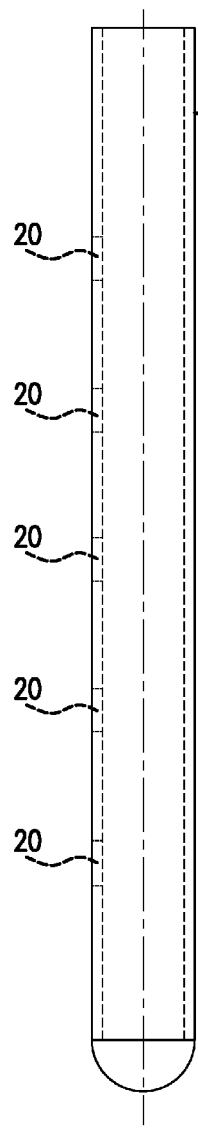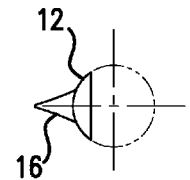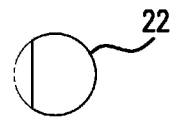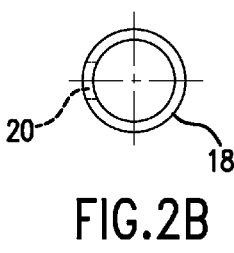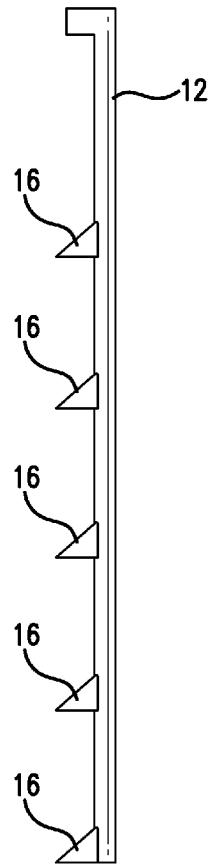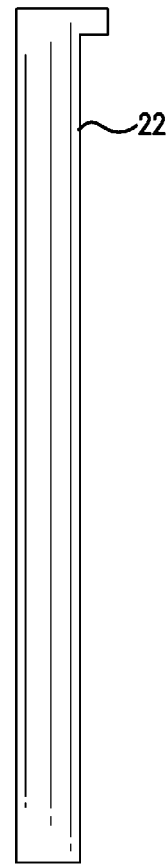

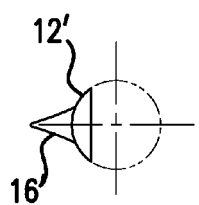
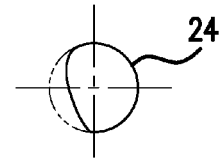
FIG.5B
FIG.6B
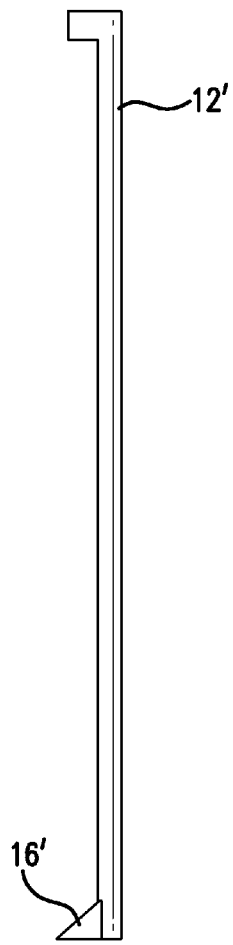
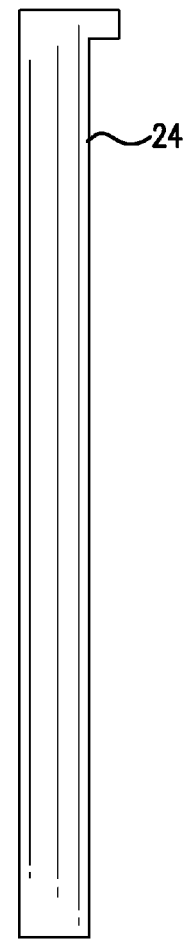
FIG.5A
FIG.6A

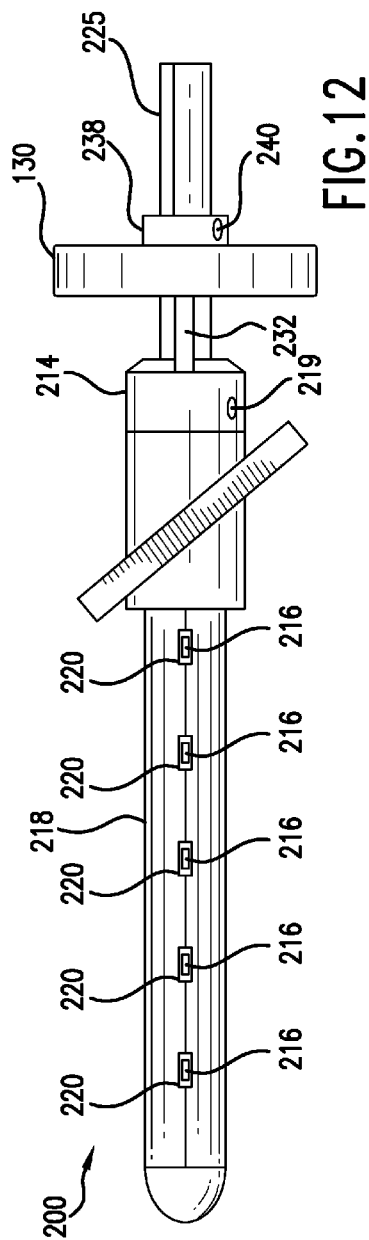
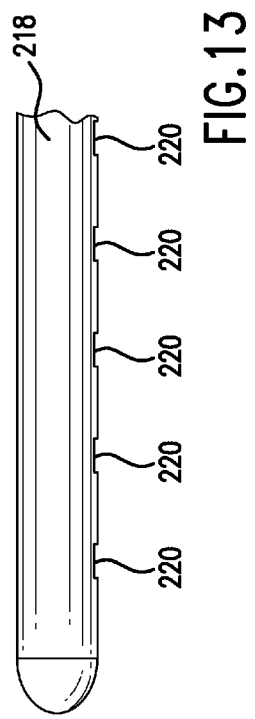
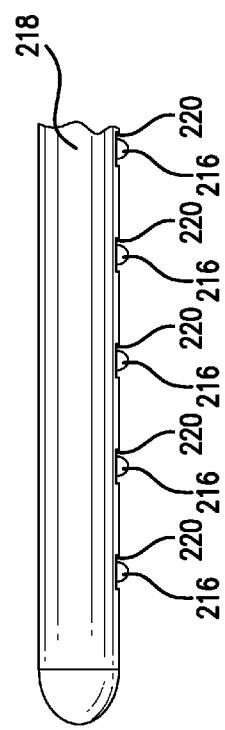
FIG. 12
FIG. 13
FIG. 14

BONE RIFLING SYSTEM AND METHOD OF PREPARING A BONE USING SUCH SYSTEM

The present application is a non-provisional utility application and claims the benefit of Provisional Application No. 61/166,128, filed Apr. 2, 2009, the contents of which are incorporated herein by reference in their entirety.

TECHNICAL FIELD

The present invention relates to new bone rifling system (BRS) and method of using such system for prosthetic bone fixation. The invention discloses a bone rifling system comprising an orthopedic undercut reamer, for use with bone cement to increase the fixation of a cemented bone implant, and also discloses a method of "rifling" the host bone. The reamer comprises a guide tube having a proximal and distal end, a cutter bar having at least one cutter extending from a portion of said cutter bar, the cutter bar positioned within the guide tube between the proximal and distal ends of the guide tube and displaceable to extend the at least one cutter from an outer surface of guide tube, an engager for engaging the cutter for controlling the displacement of said cutter bar, and a cap for closing the proximal end of the guide tube. The bone rifling system that comprises the reamer and accessories can dramatically improve prosthetic bone fixation by significantly increasing the pull out strength and decreasing the rate of clinical loosening and failure of replacement joints. Using such a system to prepare the host bone represents an improvement in prosthetic procedures.

BACKGROUND OF THE INVENTION

Prosthesis, a medical term originated from the Greek word for "addition", is an artificial extension that replaces a missing body part. In the case of an endoprosthesis, an artificial device is placed inside the body to replace the missing bodily part. This medical procedure has been widely used in many different situations. For example, endoprosthesis can be used in rebuilding joints, such as artificial hips and artificial knees. For another example, endoprosthesis has been applied to patients whose bones were amputated, including rebuilding cancer patients' limbs by creating an endoprosthetic bone and adjacent joint to replace the cancerous one.

In situations such as hip and joint replacement, wherein the prosthesis is designed to be fit or inserted into a bone, the replacements are often fixed to bones by press fitting the prosthesis into the host bone, which has been filled with bone cement such as polymethylmethracylate (PMMA). Bone cement was first used in the 1950s. Since then, some modifications have been made and alternatives have been developed to the original PMMA cement. However, the general technique that uses bone cement for prosthesis has not changed significantly in over the past 40 years. The common method of preparing the bone is to ream the bone with a bone reamer, and then inject bone cement into the medullary canal, then the prosthesis replacement is placed into the bone. The bone cement provides for an immediate fixation, similar to filling a tooth cavity. This technique always results in a smooth bore cortical host bone.

These days, millions of procedures of this type are conducted all over the world every year. However, a major clinical problem with such a system of fixing the prosthesis implant lies in the ultimate loosening of the bone-cement interface overtime.

When the implant has loosened, the prosthesis may need revision or replacement. In such case, the bone cement must be fully removed, and the prosthesis previously implanted in the body is removed and replaced by a new prosthesis. Such replacement operations usually cause loss of healthy bone substances, and are often more complex and more difficult than the original prosthesis operation. In addition, prosthesis revision operations are often more expensive for patients.

It has been found that there is rarely a loosening in the junction between the prosthesis and the cement, that is, at the prosthetic-cement junction. On the other hand, the main mechanism of loosening is the development of a loose interface between the bone and the implanted bone cement (PMMA). This problem can be solved by preparing the bone through a different method, using the new bone rifling system disclosed herein.

In using the common technique of reaming, the reaming results in the remaining bone being essentially a smooth, cortical, bony tube, with smooth internal surface, regardless of how the cement is mixed or implanted. Thus, there is minimal interdigitation of the cement into the bone. In addition, any interdigitation of the cement that may occur weakens over time, and the prosthesis is thus disconnected from the interior surface of the bone, resulting in the need to surgically reset the prosthesis.

Accordingly, there is a need to provide a system which increases prosthetic bone fixation, reliably secures the prosthesis with respect to the bone, thereby eliminating the need to conduct further surgery as the bone-cement interface does not deteriorate over time. There is also a need to use the new system to prepare the host bone in prosthesis.

SUMMARY OF THE INVENTION

A primary objective of the present invention is to provide a new bone rifling system (BRS) for unique prosthetic bone fixation. The system comprises an orthopedic undercut reamer for use together with bone cement to increase the fixation of a cemented bone implant. The bone rifling system comprises the reamer and optional accessories to cut grooves on the internal surface of a host bone before bone cement is added. The grooved internal bone surface dramatically improves prosthetic bone fixation between the bone and the bone cement, by significantly increasing the pull out strength, thus decreasing the rate of clinical loosening and failure of replacement joints. This system can be used to convert the smooth bore bone (bony tube) of the commonly reamed bone to a grooved or rifled endosteal surfaced bony tube.

In one embodiment of the invention, the disclosed new bone rifling system comprising the undercut reamer can cut controlled, deep, internal groove circles on the internal surface of a host bone.

In another embodiment of the invention, the disclosed bone rifling system comprising the reamer can cut spiral grooves analogous to standard rifle grooves on the internal surface of a host bone.

The undercut reamer is an instrument that can be used in orthopedic surgery, to create one or multiple undercuts (negative ridges) in the bone to provide enhanced fixation for endoprosthetic implants which utilize bone cement such as PMMA. The new bone rifling system (BRS) disclosed presently applies the undercut reamer to provide a grooved internal bone surface for device implantation, thus improves the integrity of the bone fixation. Specifically, the undercut surface prepared by the BRS strengthens bone-cement interface, thereby increases the pull out strength of the implant. Compared to the smooth internal surface of bone, prepared by the traditional method, the new BRS system can reduce incident of loose interface between the bone and the implanted bone cement such as PMMA, thus benefits patients who undergo prosthetic procedures. This improvement is accomplished by creating a positive lock for the fixation material into the bone.

Further, the invention provides a method of preparing a host bone for prosthesis, using the bone rifling system (BRS) disclosed in the present invention. The method can improve prosthetic bone fixation and decrease the rate of clinical loosening and failure in endoprosthesis, by significantly increasing the pull out strength, through converting smooth bore bone to a grooved or rifled bony tube. The method comprises using the BRS comprising unique orthopedic undercut reamer and optional accessories to cut circular or spiral grooves on the internal surface of host bone, then retract the reamer before adding cement to the bone, to increase fixation between the bone and the cement, for endoprosthetic implants which utilize bone cement such as PMMA.

In one embodiment of the disclosed bone preparation method, the undercut reamer can cut controlled, deep, internal groove circles on the internal surface of a host bone.

In another embodiment of the disclosed bone preparation method, the undercut reamer can cut spiral/rifling grooves analogous to standard rifle grooves on the internal surface of a host bone.

The disclosed bone rifling system allows the reamer to be placed into the intramedullary canal. The reamer includes a cutter in the form of cutting teeth. Once the reamer is positioned correctly, the cutting teeth can be extended to engage the internal bone surface. Once the cutting teeth are extended a drive mechanism is mounted on the portion of the undercut reamer outside of the bone (such as a universal adapter) so that the cutter can be rotated by hand or external power, thereby creating the undercuts at the level of the cutting teeth. This bone rifling system has an additional mechanism which permits the bone debris formed by the undercut reaming or rifling to be continuously irrigated and suctioned to remove all debris. This mechanism permits accurate and safe reaming (i.e. to avoid stress fractures) during the undercutting process. Once completed, the drive mechanism is removed and the cutting teeth are retracted and disengaged from the internal bone surface, allowing the undercut reamer to be removed from the bone without disturbing the undercuts (negative ridges) created by the reamer. Once the bone rifling system is removed from the bone, it can be completely disassembled, cleaned and sterilized. Additional one or more of the components of the system may be disposable, particularly the cutter.

The undercut reamer used in carrying out the improved prosthesis procedure consists of multiple components. A cutter may be comprised of multiple cutting surfaces (teeth) that may be angled away from a cap. The cutter may fit within a guide tube, and contain pins that can slide through the side openings of the guide tube to allow the cutter to move inside the guide tube in a controlled path. The guide tube has a slim cylinder shape that allows it to be inserted into the medullary canal of various length, for example, for long bones such as the humerus, tibia or femur. The multiple cutting surfaces (teeth) align with openings on the guide tube for the cutting teeth to extend through in order to engage with the internal surface of bones. Once the cutting teeth are engaged, the universal adapter on the end of the reamer, which stays outside of the bone, can be connected to an outside power source, to rotate the cutter, which allows the cutting teeth on the cutter to create grooves on the engaged bone surface. The grooves can be either circular or spiral, depending on how the reamer is positioned and used during the cutting process. After the undercut is created, the cutting teeth are then retracted through the openings The angled cutting teeth may assist in the removal of the cutter. The cutter can either be single use/disposable or multi-use. In either case the cutter is to be made of a sterilizable material such as cobalt chrome or other known material.

A cutter extension tube or mechanism to extend the cutter into the bone can consist of several different mechanisms so as to extend the cutter component into the bone. One example would be a rod having a D shaped cross-section, which fits within the guide tube, with the flat portion mating up against the cutter. When the D shaped rod is forced down into the guide tube, the multiple cutting surfaces are pushed into the bone. Removal of the D shaped rod allows the cutter to be removed. Alternatively, a cam shaped rod, which fits within the guide tube having an increasing cross-section initially allows the cutter to be inserted with ease. Once the cutter is in place the cam shaped rod is turned to apply pressure to the cutter and the opposite sidewall of the tube, allowing the cutting surfaces to be extended into the bone. Once the undercuts are completed the cam shaped rod would be turned to remove the force against the cutter and would allow the cutter to be retracted and removed from the tube. In another option, the cutter bar can be a flat plate that is positioned between two semi-cylinders, with the plate of the cutter bar including pins extending therefrom which engage slots or openings in the semi-cylinders which act as cam surfaces to extend the cutter blades from a side of the guide tube. When the cutter bar is pushed by force, the pins can move through the guide tube as directed by the slots, which allows the cutter bar to move radially away from a central axis of the guide tube towards the periphery of the guide tube, thus allowing the cutting teeth to extend out through openings on the guide tube.

A pressurized membrane, which fits within the guide tube, could also be employed. With the membrane deflated the cutter can be placed within the tube. Once the cutter is in place, the membrane would be pressurized and filled with a saline solution. As the pressure of the membrane against the cutter increases, the cutter will be extended into the bone. Once the undercuts are completed the membrane would be decompressed and would allow the cutter to be retracted from the bone and removed from the tube.

The guide tube is provided to allow proper placement of the cutter within the intramedullary canal. The guide tube will come in multiple diameters and lengths to enable appropriate sizing for multiple size canals. The guide tube is provided with openings to allow the cutting teeth to be extended and retracted through the tube, thus helping the reamer to get into and out of the bone. The guide tube may also contain a continuous suction-irrigation tube as well as an external port and connection therein to permit the extraction of debris from the cutting process. The continuous suction-irrigation system being similar to those currently used in connection with various bone reaming devices.

In an initial embodiment, a cap is mechanically fastened to the guide tube once the cutter has been extended into the bone, locking the cutter in place. The external portion of the cap will include a shank/quick disconnect allowing use with variable power assisted and manual drills. Alternatively, the external portion of the reamer will include an engager which can be pushed toward the cap to apply pressure on the cutter bar and move the cutter bar inside the guide tube to make the cutting teeth extend out. The external portion of the reamer will also include a universal adapter that can be connected to outside power source to rotate the cutter for cutting the internal surface of bone. Once the cutting teeth are extended through the openings of the tube and engage to the internal surface of bone, the guide tube and cutter are rotated to cut either the "O" ring grooves or spiral grooves into the interior surface of the bone. After the undercut reamer has been extended into the bone and the cuts made, the cap is unfastened from the guide tube allowing the extension mechanism and cutter to be retracted from the guide tube and the guide tube to be retracted from the bone; or the engager is released and moves away from the cap to allow the cutting teeth to retract.

A detailed description is given in the following embodiments with reference to the accompanying drawings. Advantages and features of the present invention will become more apparent from the following detailed description of the present invention when viewed in conjunction with the drawings.

BRIEF DESCRIPTION OF THE DRAWINGS

Embodiments of the invention will now be described, by way of example only, with reference to the accompanying schematic drawings in which corresponding reference symbols indicate corresponding parts.

FIG. 1A is a partial cross-sectional view and FIG. 1B is a lateral cross-sectional view of the undercut reamer in accordance with the present invention.

FIGS. 2A and 2B are side and end views of the guide tube.

FIGS. 3A and 3B are side and end views of the cutter in accordance with one embodiment of the invention.

FIGS. 4A and 4B are side and end views of the extension tube mechanism in accordance with one embodiment of the invention.

FIGS. 5A and 5B are side and end views of the cutter in accordance with another embodiment of the invention.

FIGS. 6A and 6B are side and end views of the extension tube mechanism in accordance with another embodiment of the invention.

FIG. 12 is a side view of the bone rifling system (BRS) of the present invention.

FIG. 13 is an expanded view of the guide tube of the bone rifling system (BRS) of the present invention in the unengaged state.

FIG. 14 is a further expanded view of the guide tube of the bone rifling system (BRS) of the present invention in the engaged state wherein the cutting teeth extend out through openings in the guide tube of the undercut reamer.

DETAILED DESCRIPTION OF THE PREFERRED EMBODIMENT

Figure 7:
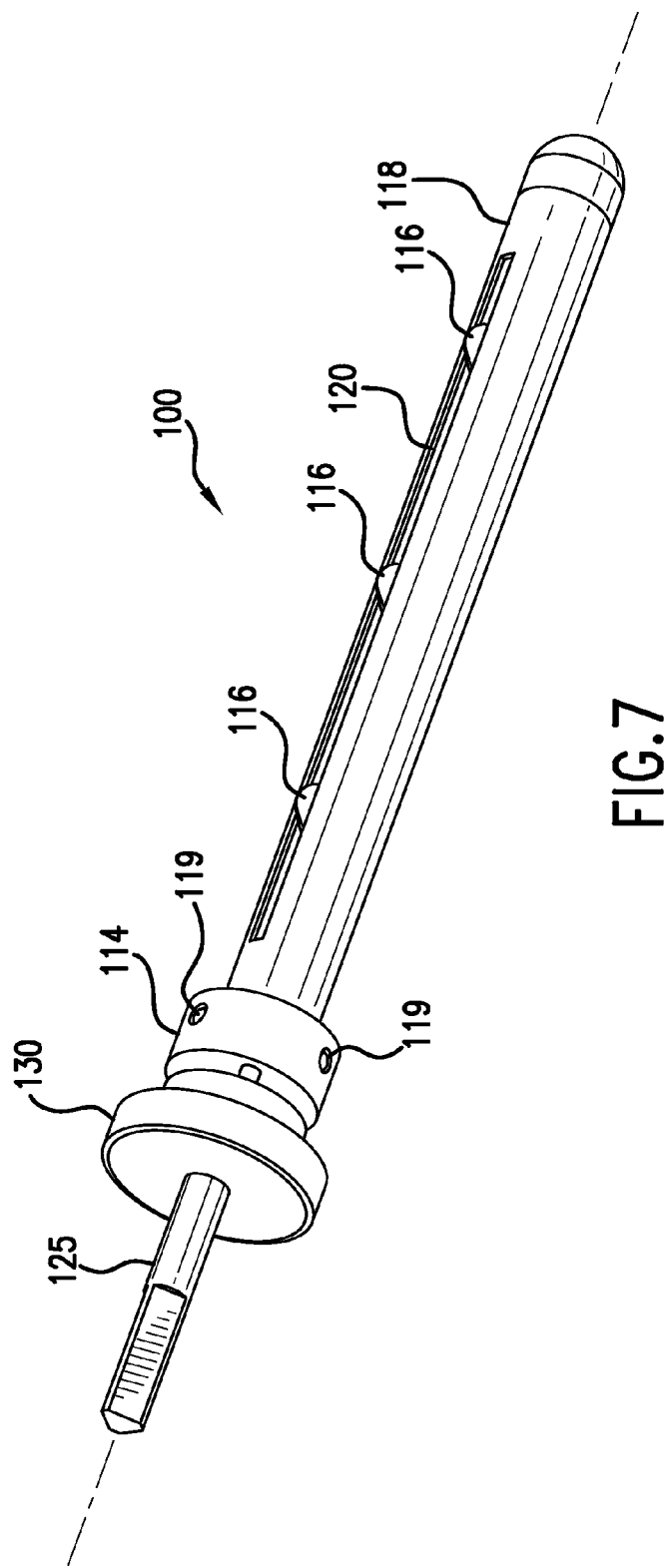
FIG. 7 is a perspective view of the undercut reamer assembly in accordance with an alternative and preferred embodiment of the present invention.

As noted hereinabove, by forming controlled, deep, internal ridges on the host bone by way of a series of internal 'O' rings or a spiral/rifling groove using an undercut reamer and its system of use will increase dramatically the pull out strength and decrease the rate of clinical loosening and failure of replacement joints. This technique converts the smooth bore bone (bony tube) of the commonly reamed bone to a grooved or rifled endosteal surfaced bony tube.

In accordance with the present invention as illustrated in FIGS. 1-6, the undercut reamer 10 is an instrument to be used in orthopedic surgery, to create one or multiple undercuts (negative ridges) in the bone to provide enhanced fixation for endoprosthetic implants which utilize bone cement. Providing an undercut surface for device implantation improves the integrity of the bone/prosthetic fixation; specifically, the bone-cement interface, thereby increasing the pull out strength of the implant. This is accomplished by creating a positive lock for the fixation of material into the bone.

The bone rifling system and method of preparing a bone using such system includes an undercut reamer 10 which consists of multiple components, and allows the reamer to be placed into the intramedullary canal and once positioned correctly, has cutters 12 that are extended into the bone. Once the cutters 12 are extended, a chuck 14 is mounted on the portion of the undercut reamer outside of the bone so that it can be rotated by hand or power thereby creating the undercuts at the level of the cutters. This tube may have an additional mechanism which permits the bone debris formed by the undercut reaming or rifling to be continuously irrigated and suctioned to remove all debris (not shown). This permits accurate and safe reaming (i.e. to avoid stress fractures) during the undercutting process. Once completed, the chuck 14 is removed and the cutters 12 are extracted allowing the undercut reamer 10 to be removed without disturbing the undercuts (negative ridges) created by the reamer. Once the total undercut reamer construct is removed from the bone, it can be completely disassembled, cleaned and sterilized. Such disassembly could include the guide tube being divided into two halves. Further, one or more of the components of the undercut reamer may be disposable, particularly the cutters 12.

The undercut reamer 10 used in carrying out the method consists of multiple components. The cutter 12 may be comprised of multiple cutting surfaces 16 that are angled away from the cap 14 and fit within a guide tube 18 which has been inserted into the medullary canal of various length long bones such as the humerus, tibia or femur. The multiple cutting surfaces 16 align with holes or openings 20 in the guide tube, which provide an opening for the cutting surfaces to extend through. Once the undercut is created the cutting surfaces 16 are then retracted through the guide holes 20. The angled cutting surfaces assist in the removal of the cutter. The cutter can either be single use/disposable or multi-use. In either case the cutter is to be of a sterilizable material such as cobalt chrome or other known material.

Alternatively, the undercut reamer 10 may include a cutter 12' as illustrated in FIGS. 5A and 5B. The cutter 12' includes only a single cutter surface 16' which extends at an angle such that as the undercut reamer is rotated and withdrawn from the bone, the cutter surface 16' forms a spiral or rifle groove in the interior surface of the bone.

A cutter extension tube or mechanism to extend the cutter into the bone may consist of several different mechanisms so as to extend the cutter component into the bone. One example would be a rod 22 having a D shaped cross-section illustrated in FIGS. 4A and 4B, which fits within the guide tube 18, with the flat portion mating up against the cutter as shown in FIG. 1A. The D-shaped rod 22 is sized such that when the D shaped rod 22 is forced down into the guide tube 18, the multiple cutting surfaces 16 are pushed into the bone. Removal of the D shaped rod 22 allows the cutter to be removed. Alternatively, a cam shaped rod 24 as shown in FIG. 6A and 6B, which fits within the guide tube having an increasing cross-ssection initially allows the cutter to be inserted with ease. Once the cutter is in place the cam shaped rod 24 is turned to apply pressure to the cutter and the opposite sidewall of the tube, allowing the cutting surfaces to be extended into the bone. Once the undercuts are completed the cam shaped rod 24 would be turned to remove the force against the cutter and would allow the cutter to be retracted and removed from the tube.

A pressurized membrane (not shown), which fits within the guide tube could also be employed. With the membrane deflated the cutter can be placed within the tube. Once the cutter is in place, the membrane would be pressurized and filled with a saline solution. As the pressure of the membrane against the cutter increases, the cutter will be extended into the bone. Once the undercuts are completed the membrane would be decompressed and would allow the cutter to be retracted from the bone and removed from the tube.

The guide tube 18 is provided to allow proper placement of the cutter 12 within the intramedullary canal. The guide tube 18 will come in multiple diameters and lengths to enable appropriate sizing for multiple size canals. The guide tube will be provided with at least one and likely multiple openings 20 to allow the cutters to be extended and retracted through the tube and into and out of the bone. The guide tube 18 will also contain a continuous suction-irrigation tube as well as an external port and connection therein to permit the extraction of debris from the cutting process. The continuous suction-irrigation system (not shown) being similar to those currently used in connection with various bone reaming devices.

The cap 14 is mechanically fastened to the guide tube once the cutter has been extended into the bone, locking the cutter in place. The external portion of the cap will include a shank/quick disconnect 26 allowing use with variable power assisted and manual drills (not shown). Once the cutter extensions are extended into the bone, the guide tube 18 and cutters 16 are rotated to cut the "O" ring grooves or rifling into the interior surface of the bone. After the undercuts have been extended into the bone and the cuts made, the cap is unfastened from the guide tube allowing the extension mechanism and cutter to be retracted from the guide tube and the guide tube to be retracted from the bone. Alternatively, when using the rifling cutter 12' as shown in FIGS. 5A and 5B, the guide tube 18 may be withdrawn from and inserted into the bone as the guide tube 18 and cutter 16' are rotated to form a substantially continuous spiral/rifle groove in the inner bone surface.

As noted hereinabove, by cutting controlled internal ridges and grooves on the host bone, the bone rifling system (BMS) converts the smooth bore internal surface of the commonly reamed bone (bony tube) to a grooved or rifled endosteal surfaced bony tube. The system comprises an orthopedic undercut reamer that can be used to cut the grooves on bones to increase the fixation between the bone and the cement, thus prevent loosening of cemented bone implant. The bone rifling system that comprises the reamer and optional accessories can dramatically improve prosthetic bone fixation by significantly increasing the pull out strength and decreasing the rate of clinical loosening and failure of replacement joints.

In accordance with the present invention, the undercut reamer 10 is an instrument to be used in orthopedic surgery, to create one or multiple undercuts (negative ridges) on the internal surface of bone to provide enhanced fixation for endoprosthetic implants which utilize bone cement. Providing an undercut surface for device implantation improves the integrity of the bone/prosthetic fixation, specifically the fixation of the bone-cement interface. Therefore, the disclosed new bone rifling system increases the pull out strength of the implant by creating a positive lock for the fixation of material into the bone.

A preferred embodiment of the present invention will now be discussed with respect to FIG. 7-14. As illustrated in FIG. 7, the preferred Bone Riffling System (BRS) includes a bone undercut reamer 100 having a guide tube 118. In accordance with the preferred embodiment, and particularly the undercut reamer of FIGS. 7 and 8, the cutter bar 110 is a flat bar that fits within the guide tube 118 and includes pins 140, 141 that fit within the openings or cam slots 117 formed in positioning semi-cylinders 142, 143. The slots 117 will be discussed in greater detail hereinbelow with reference to FIG. 9. When the semi-cylinders 142, 143 are pushed by force, the pins on the cutter bar move through the guided path as directed by the cam slots 117, which allows the cutter bar 110 to move away from the central axis of the guide tube 118 towards the peripheral edge of the tube, thus forcing the cutting teeth 116 to extend out through opening(s) 120 formed in the guide tube 118.

The guide tube 118 is provided to allow proper placement of the cutter bar 110 within the intramedullary canal. The guide tube 118 may come in multiple diameters and lengths to enable appropriate sizing for multiple size canals. The guide tube 118 will be provided with at least one and likely multiple openings 120 to allow the cutters 116 of the cutter bar 110 to be extended and retracted through the guide tube 118 and into and out of the bone. Like the previous embodiment, the guide tube 118 may also contain a continuous suction-irrigation tube as well as an external port and connection therein to permit the extraction of debris from the cutting process. The continuous suction-irrigation system (not shown) being similar to those currently used in connection with various bone reaming devices.

Figure 8:
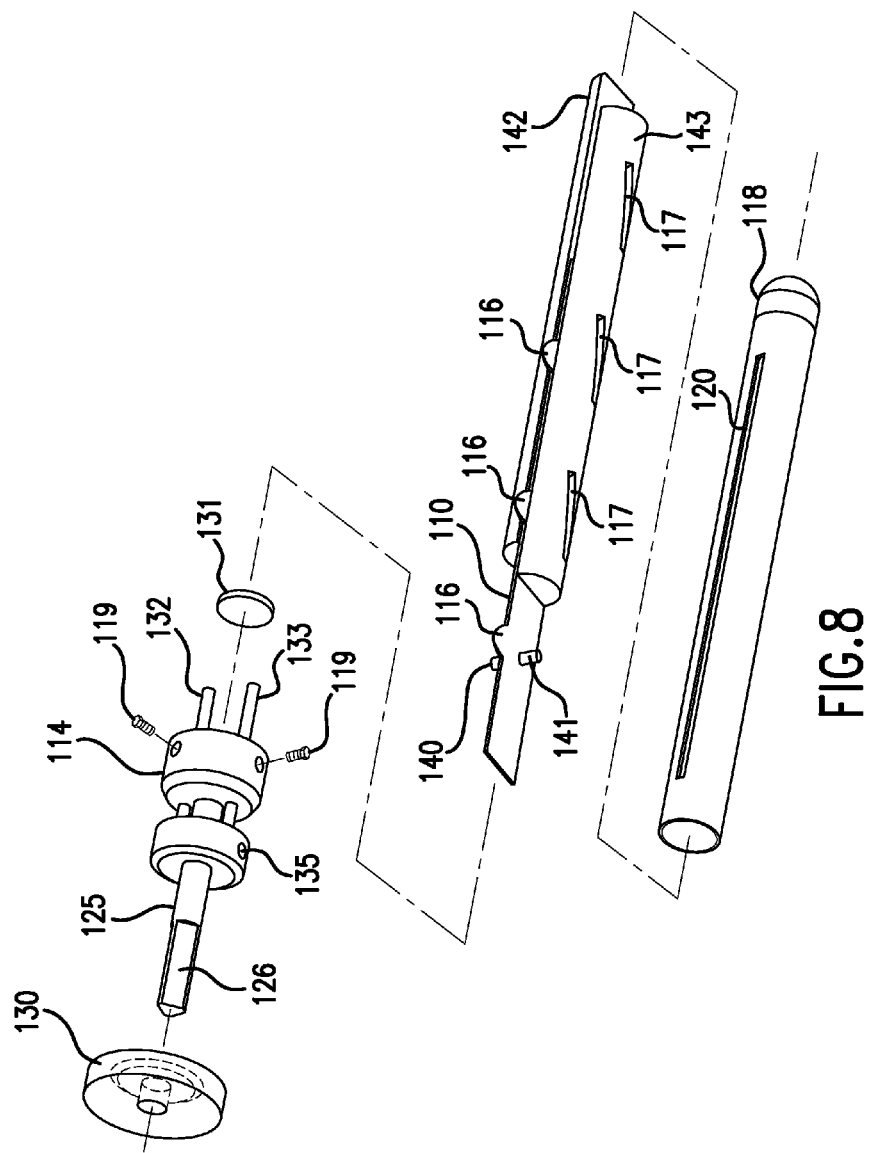
FIG. 8 is an exploded perspective view of the internal structure of the undercut reamer of FIG. 7.

The undercut reamer 100 illustrated in FIGS. 7 and 8 includes a cap 114 which is mechanically fastened to the guide tube 118 by way of one or more hex set screws 119. The cap 114 is secured to and may be formed integral with a shank 125 and slidably received a pair of engager rods 132, 133, the significance of which will be explained in greater detail hereinbelow. Formed on an extended portion of the shank 125 is a surfaced area 126 which receives a quick connect of a drive device (not shown). This drive device may be a variable power assisted or manual drill (again, not shown).

The engager rods 132, 133 are secured to or formed integrally with an engager 130. The engager 130 may be of an enlarged disc which allows for ease in pushing the engager rods 132, 133 through the cap 114 and into contact with the semi-cylinders 142, 143 in order to displace the semi-cylinders 142, 143 toward a distal end of the guide tube 118. A force dispersing disc 131 may be positioned between the ends of the engager rods 132, 133 and the end surface of the semi-cylinders 142, 143 in order to better transfer the force exerted by the engager rods 132, 133 to the semi-cylinders 142, 143 to aid in the simultaneous movement of the semi-cylinders 142, 143 through the guide tube 118. Once the engager rods 132, 133 are fully inserted into the guide tube 118 through the cap 114, the engager is secured in place by way of at least one hex set screw 135. In doing so, the semi-cylinders 142, 143, maintain the cutters 116 of the cutter bar 110 in the extended position. Once the cutters 116 are extended into the bone, the guide tube 118 and cutters 116 are rotated to cut "O" ring grooves or rifling into the interior surface of the bone. After the undercuts have been formed in the bone, the engager is released by unscrewing the hex set screw 135 which permits the engager rods 132, 133 to be retracted from the guide tube 118 and thus permits the semi-cylinders 142, 143 to return to their original position due to a force from a coil spring 150 (discussed in greater detail hereinbelow) thereby retracting the cutters 116 from the bone and back into the guide tube 118 due to the influence of the cam slots 117 on the pins 140, 141. Thereby permitting the guide tube to be readily removed from the intramedullary canal. Alternatively, when it is desired to form a spiral undercut in the bone, the undercut reamer 110 may be retracted during the rotation of the reamer and stopped where desired. If the reamer is not fully rotated out of the intramedullary canal, the above procedure of retracting the cutters 116 can be carried out at any time to remove the reamer from the intramedullary canal.

As shown in FIG. 8, and as discussed hereinabove, the external portion of the reamer 100 includes an engager 130 having a pair of engager rods 132, 133 which extend through the cap 114 and into the guide tube 118, to apply pressure on the semi-cylinders 142, 143, and move the cutter bar 110 inside the guide tube to force the cutters 116 to extend out through the opening(s) 120. Once the cutters 116 are extended through the opening(s) 120 of the guide tube 118 and engage to the internal surface of the intramedullary canal of the bone, the guide tube 118 and cutters 116 are rotated to cut either the "O" ring grooves or spiral grooves into the interior surface of the bone.

Figure 9:
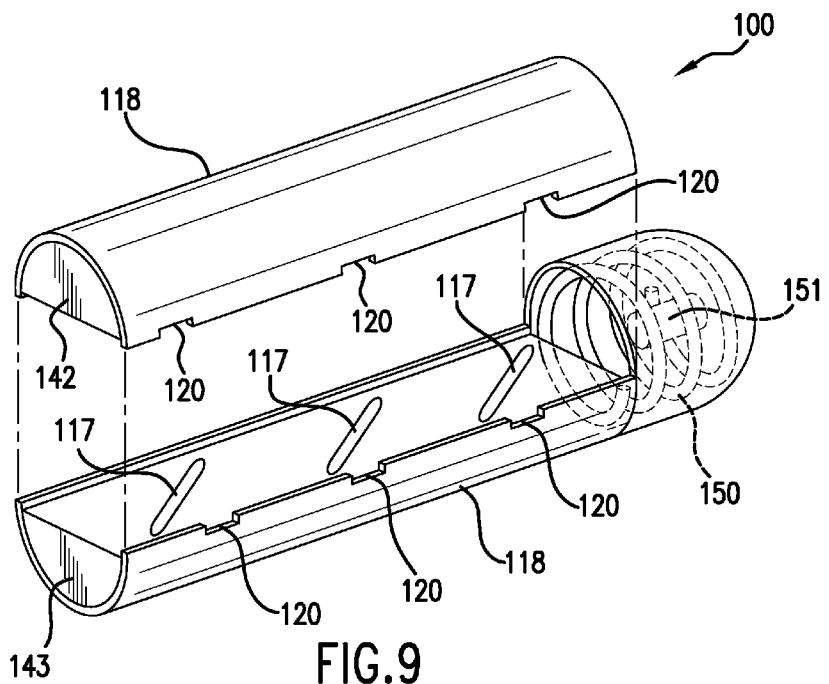
FIG. 9 is a cross-sectional view of a portion of the interior of the undercut reamer of FIG. 7.

The internal structure of the reamer 100 is further illustrated in FIG. 9, which shows a partial cross-sectional view of the undercut reamer 100. Specifically, the undercut reamer 100 is cut-in-half through the elongated axis, with the top half removed to reveal the internal structure. In particular, FIG. 9 shows the guide tube 118 and one of the semi-cylinders 142. As is readily apparent from FIG. 9, the semi-cylinder 142 includes a plurality of cam slots 117 which are formed therein and receive the pins 140, 141 of the cutter bar 110 (not shown). As can be appreciated, because the cam slots 117 are positioned at an angle with respect to the central axis of the guide tube 118, as the semi-cylinders 142, 143 are moved in the axial direction of the guide tube 118, the pins 140, 141 of the cutter bar 110 will be driven towards the periphery of the guide tube 118 thus forcing the cutters 116 towards the periphery of the guide tube 118 and out through the opening(s) 120 formed therein. Also shown in FIG. 9 is the coil spring 150. The specific structure of the coil spring 150 will be discussed in greater detail hereinbelow with respect to FIG. 11.

Figure 10:
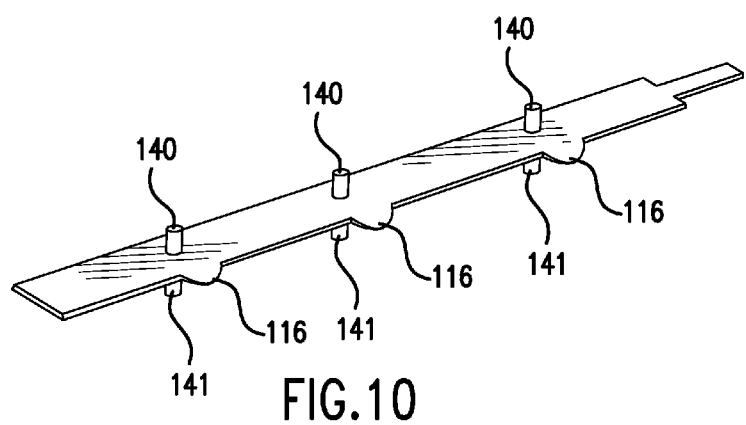
FIG. 10 is a perspective view of a cutter bar to be positioned in the undercut reamer of FIG. 7.

A perspective view of the cutter bar 116 is shown in FIG. 10. The figure shows 3 sets of pins 140, 141 and 3 cutters 116. As can be ready appreciated, any number of pin sets and cutters can be used and the number of pin sets need not equal the number of cutters. Further, while the pins are illustrated as being in sets extending collinear with one another, the sets may be offset from one another or even extend from only one side of the cutter bar 110. Additionally, and end 146 of the cutter bar 110 is of a reduced dimension. This enables the end 146 to extend beyond the semi-cylinders and through the coil spring 150 and into contact with a stop 151 positioned in the distal end of the guide tube 118. This feature will be explained in greater detail hereinbelow with respect to FIG. 11.

Figure 11:
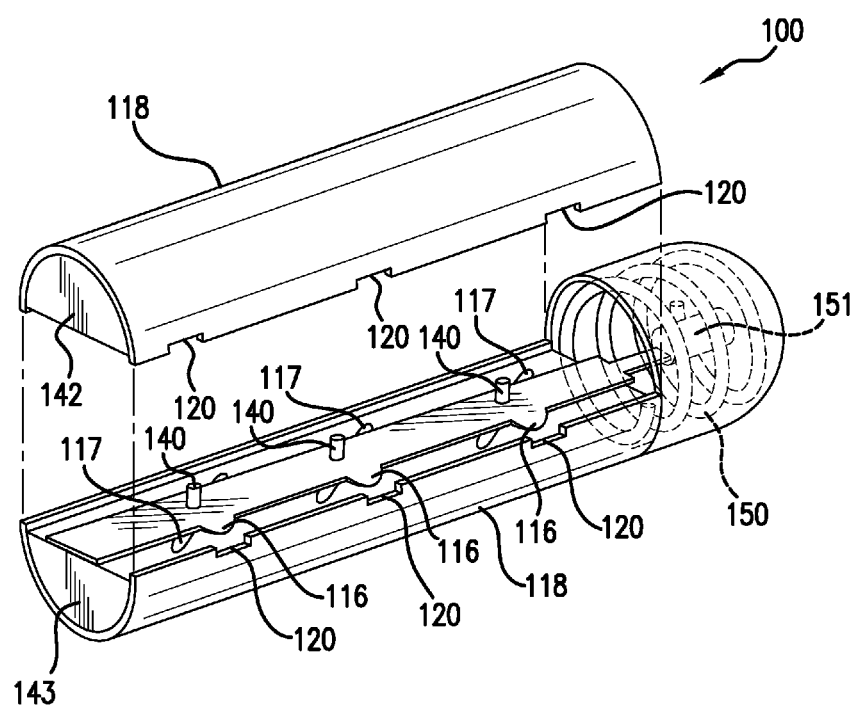
FIG. 11 is a schematic side view of the spring-assist for the cutting teeth extension structure of the present invention.

The semi-cylinders 142 and 143 as well as the cutter bar 110 can only move within a limited range inside the guide tube 118. FIG. 11 is a perspective view of the guide tube 118 in an opened-up condition similar to FIG. 9 including the cutter bar 110 positioned therein. The spring assist mechanism includes the coil spring 150 and stop 151. The semi-cylinders 142, 143 are displaced within the guide tube 118 and positioned against the spring assist mechanism and particularly the coil spring 150. The coil spring 150 resists movement of the semi-cylinders 142, 143 inside the guide tube 118 when the semi-cylinders are moved towards the distal end of the guide tube 118. The coil spring 150 also provides a force for directing the semi-cylinders 142, 143 away from the distal end of the guide tube 118 when the cutters 116 are to be retracted into the guide tube 118 for removal of the device.

As noted from FIG. 11, the reduced end 146 of the cutter bar 110 is positioned in contact or at least close proximity to the stop 151 and the pins 140 are positioned within the slots 117. In doing so, when a force is applied to the semi-cylinders 142, 143 in the axial direction of the guide tube 118, the reduced end 146 of the cutter bar 110 contacts the stop 151 to prevent axial movement of the cutter bar 110 such that the cutter bar 110 is moved laterally toward the periphery of the guide tube 118 by way of the pins 140, 141 which move through corresponding cam slots 117 formed in the semi-cylinders 142, 143. As a result, when the engager is pushed down, the cutter bar 110 moves laterally within the guide tube 118 and towards the periphery of the tube, thereby the cutters 116 on the cutter bar 110 extend out through the opening(s) 120 of the guide tube 118.

As with most surgical instruments, a majority of the undercut reamer 100 is made of stainless steel. However, any known material which is of sufficient strength to endure the stress placed on the device when in use and that can be readily cleaned and sterilized after each use may be employed. Such disassembly could include the guide tube 118 being divided into two halves. Further, one or more of the components of the undercut reamer may be disposable, particularly the cutter bar 110.

Similar to the device illustrated in FIGS. 7-11, FIGS. 12-14 illustrate a slightly modified embodiment of the present invention. Similar to that discussed above, the undercut reamer 200 is formed primarily of stainless steel; however, other known materials which are of sufficient strength to endure the stress placed on the device when in use and that can be readily cleaned and sterilized after each use may be used. Such disassembly could include the guide tube being divided into two halves. FIG. 12 illustrates the undercut reamer 200 of the bone rifling system (BRS) in accordance with the present invention. Like the device of FIG. 7, the undercut reamer 200 set forth in FIGS. 12-14 includes multiple components which allow the reamer to be placed into the intramedullary canal and once positioned correctly, can cut either circular or spiral undercuts in the inner wall of the bone. The undercut reamer 200 includes a guide tube 218. In accordance with this embodiment, the components positioned in the interior of the guide tube 218 are substantially identical to those discussed with respect to FIGS. 7-11. Particularly, the undercut reamer 200 of FIGS. 12-14 includes a cutter bar which is a flat bar that fits within the guide tube 218 and includes cutters 216 and pins that fit within the openings or cam slots formed in positioning semi-cylinders. As with the previous embodiment, when the semi-cylinders are pushed by force toward the distal end of the device, the cutter bar is maintained in its axial position and the pins of the cutter bar move through the guided path as directed by the cam slots, which allow the cutter bar to move away from a central axis of the guide tube 218 towards the peripheral edge of the guide tube 218, thus forcing the cutters 216 from the retracted position illustrated in FIG. 13 to the extended position illustrated in FIG. 14, wherein the cutters 216 to extend out through openings 220 formed in the guide tube 218.

Like the previous embodiment, the guide tube 218 is provided to allow proper placement of the cutter bar within the intramedullary canal. The guide tube 218 may come in multiple diameters and lengths to enable appropriate sizing for multiple size canals. The guide tube 218 is provided with multiple openings 220 to allow the cutters 216 of the cutter bar to be extended and retracted through the guide tube 218 and into and out of the bone. Like the previous embodiment, the guide tube 218 may also contain a continuous suction-irrigation tube as well as an external port and connection therein to permit the extraction of debris from the cutting process. The continuous suction-irrigation system (not shown) being similar to those currently used in connection with various bone reaming devices.

The undercut reamer 200 illustrated in FIG. 12 includes a cap 214 which is mechanically fastened to the guide tube 218 by way of one or more hex set screws 219. The cap 214 is secured to and is preferably formed integrally with a shank 225. The cap 214 slidably receives a pair of engager rods 232, 233, the significance of which is similar to that of the previous embodiment and will be explained in greater detail hereinbelow. The free end of the shank 225 receives a quick connect of a drive device (not shown). This drive device may be a variable power assisted or manual drill (again, not shown).

The engager rods 232, 233 are secured to or formed integrally with an engager 230. The engager 230 may be of an enlarged disc which allows for ease in pushing the engager rods 232, 233 through the cap 214 and into contact with the semi-cylinders positioned inside the guide tube 218 in order to displace the semi-cylinders toward a distal end of the guide tube 218. A locking ring 238 is also positioned on the shank 225 in order to maintain the cutters in their extended position. The locking ring 238 includes at least one hex set screw received in screw hole 240 in order to maintain the position of the locking ring 238 along the shank 225. A force dispersing disc (not shown) may be positioned between the ends of the engager rods 232, 233 and the end surface of the semi-cylinders in order to better transfer the force exerted by the engager rods 232, 233 to the semi-cylinders to aid in the simultaneous movement of the semi-cylinders through the guide tube 218.

The enlarged disc forming the engager 230 may be of a single piece or of a two piece construction wherein the engager 230 has an inner disc which is fixedly secured to the engager rods 232, 233 and an outer disc which rotatably receives the inner disc. In doing so, during the rotation of the undercut reamer device 200, the outer disc can be held stationary thereby leaving the inner disc which is integral with the engager rods 232, 233 which are extend through the cap 214 and into the guide tube 218 to rotate as directed by the power assist mechanism or manual drill. A handle 244 may also be positioned on the guide tube 218 to assist in manipulating the device.

In use, the undercut reamer 200 and particularly the guide tube 218 of the undercut reamer 200 is inserted into the intramedullary canal. During this insertion, the cutters 216 are in the retracted position. Once the guide tube is properly positioned within the intramedullary canal, the engager rods 232, 233 are forced into the guide tube 218 through the cap 214 by pushing forward on the engager 230. Once the engager rods 232, 233 are extended a desired distance into the guide tube 218 and the cutters are extended a desired distance from the guide tube 218, the engager 230 is secured in place by way of the locking ring 238 by the hex set screw. In doing so, the semi-cylinders, maintain the cutters 216 of the cutter bar in the extended position. Once the cutters 216 are extended into the bone, the guide tube 218 including the cutters 216 are rotated to cut "O" ring grooves or rifling into the interior surface of the bone. It should be noted that the distance in which the cutters 216 extend from the guide tube 218 is dependent on both the length of the cutters 216 as well as the distance in which the semi-cylinders are displaced in the axial direction of the guide tube 218. This displacement may also be controlled by the distance in which the engager rods 232, 233 are inserted into the guide tube. Accordingly, the user may readily adjust the amount of penetration the cutters 216 make into the intramedullary canal.

After the undercuts have been formed in the intramedullary canal of the bone, the engager 230 is released by unscrewing the hex set screw maintaining the locking ring 238 in place, which permits the engager rods 232, 233 to be retracted from the guide tube 218 and thus permits the semi-cylinders to return to their original position due to a force from a coil spring positioned in the distal end of the guide tube 218, similar to that illustrated in FIG. 11. In doing so, the cutters 216 are retracted from the bone, back into the guide tube 218 due to the influence of the cam slots of the semi-cylinders and the pins of the cutter bar, similar to that of the previous embodiment, thereby permitting the guide tube to be readily removed from the intramedullary canal. Alternatively, when it is desired to form a spiral undercut in the bone, the undercut reamer 200 may be retracted during the rotation of the reamer and stopped where desired. If the reamer is not fully rotated out of the intramedullary canal, the above procedure of retracting the cutters 216 can be carried out at any time to remove the reamer from the intramedullary canal.

The present invention also provides a method for unique prosthetic bone fixation using the disclosed new bone rifling system (BRS). The method comprises the steps of using the BRS to cut circular or spiral grooves on the internal surface of the bone, remove the reamer and also remove the debris generated during the cut, placing a desired implant in the bone, and placing cement in the bone to secure the implant to the bone. More specifically, the method comprises inserting the orthopedic undercut reamer into the desired location inside the bone, pushing the engager by hand or using other means to move the engager rods forward to force the cutter bar laterally through the guide tube by forcing the pins of the cutter bar to move through the guided path formed by the slots in the semi-cylinders to extend the cutters through openings formed in the guide tube, engage the cutting teeth with the internal surface of the bone, connect a universal adapter to a power source, rotate the cuter bar to allow the cutting teeth to cut grooves on the internal surface of the bone, continuously irrigating and suctioning the debris formed by the undercut reaming or rifling to permit accurate and safe reaming and avoid stress fractures during the undercutting process. Then retracting the cutters to disengage from the bone after the cutting is complete, allowing the undercut reamer to be removed without disturbing the undercuts (negative ridges) created by the reamer, and finally placing a desired implant in the bone and placing cement in the bone to secure the implant to the bone.

While the foregoing invention is described with reference to several embodiments, the present invention may be practiced otherwise without departing from the spirit and scope of the invention. While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

I claim:

1. A method of preparing bone for a prosthesis, comprising:
   providing a bone rifling system for cutting circular or spiral grooves on an internal surface of a host bone, said bone rifling system including an undercut reamer, the undercut reamer having:
   a guide tube having a proximal and distal end,
   a cutter bar having at least one cutter extending from a portion of said cutter bar, said cutter bar being positioned within said guide tube between the proximal and distal ends of said guide tube and displaceable to extend said at least one cutter from an outer surface of said guide tube, an engager having at least one engagement rod and adapted to control the displacement of said cutter bar and to engage the cutter with the internal surface of the bone, and at least one semi-cylinder positioned within the guide tube and adapted to displace said cutter bar in response to movement of said at least one engagement rod;

positioning said undercut reamer within an intramedullary canal of the bone;

extending the at least one cutter from a surface of said undercut reamer;

rotating said undercut reamer and said cutter to form an undercut in the intramedullary canal of the bone;

retracting said at least one cutter to a position within the surface of said undercut reamer; and removing said undercut reamer from the intramedullary canal of the bone.

2. The method of claim 1, further comprising placing cement in the intramedullary canal of the bone to secure the implant to the bone.

3. The method of claim 1, further comprising removing debris generated during the undercutting process.

4. The method of claim 1, wherein the undercut reamer for cutting circular or spiral undercut groove in the intramedullary canal of the bone comprises:

a cap for closing the proximal end of the guide tube.

5. The method of claim 4, wherein the at least one engagement rod extends from said engager through said cap and is in contact with said at least one semi-cylinder.

6. The method of claim 5, wherein the undercut reamer includes a pair of semi-cylinders having said cutter bar positioned between said semi-cylinders and said engager includes at least two engagement rods.

7. The method of claim 6, wherein said cutter bar includes at least one guide pin and at least one of said semi-cylinders includes at least one guide slot such that said at least one guide slot receives said at least one guide pin for controlling the displacement of said cutter bar.

8. The method of claim 7, wherein said cutter bar includes a plurality of guide pins and said semi-cylinders include a corresponding number of guide slots for receiving a respective one of said guide pins for controlling the displacement of said cutter bar.

9. The method of claim 8, wherein said engagement rods engage said semi-cylinders through said cap to provide a pushing force, to displace the semi-cylinders in a substantially axial direction of the guide tube and the cutter bar in a substantially radial direction of the guide tube.

10. The method of claim 9, wherein said cap includes a shank extending therefrom away from said guide tube and a power source is capable of being connected to said shank to rotate said guide tube and cutter bar for cutting the bone.

11. The method of claim 10, wherein said engager is positioned on said shank and said engagement rods extend substantially parallel to said shank.

12. The method of claim 10, wherein the undercut reamer is capable of cutting circular grooves or spiral grooves in the internal surface of the bone to a increase fixation strength between the bone and the endoprothesis.

13. The method of claim 1, wherein said guide tube includes at least one opening in a side wall thereof for receiving said at least one cutter of said cutter bar.

14. The method of claim 13, wherein said at least one cutter extends out through said at least one opening in the guide tube exposing said at least one cutter to cut at least one groove on the internal surface of the bone.

15. The method of claim 14, wherein said at least one cutter is retractable through said at least one opening in said guide tube to disengage said cutter from the bone after cutting, allowing the reamer to be removed from the bone before placement of the endoprothesis.

* * * * *